United States Patent
Ofsthun et al.

[11] Patent Number: 5,871,649
[45] Date of Patent: Feb. 16, 1999

[54] AFFINITY MEMBRANE SYSTEM AND METHOD OF USING SAME

[75] Inventors: Norma J. Ofsthun, Rolling Meadows; Paul J. Soltys, Lake Zurich; Gretchen A. Kunas, Wauconda, all of Ill.

[73] Assignee: Baxter International Inc., Deerfield, Ill.

[21] Appl. No.: 893,472

[22] Filed: Jul. 11, 1997

Related U.S. Application Data

[62] Division of Ser. No. 668,582, Jun. 20, 1996.

[51] Int. Cl.⁶ .......................... B01D 63/02; B01D 61/00; A61M 1/34
[52] U.S. Cl. ................ 210/645; 210/321.6; 210/321.79; 210/321.8; 210/321.88; 210/321.89; 210/500.23; 210/650; 210/651; 435/181; 604/4
[58] Field of Search ..................... 210/645, 650, 210/651, 767, 321.6, 321.78, 321.79, 321.8, 321.87, 321.88, 321.89, 500.22, 500.23; 604/4, 5, 6; 435/177, 180, 181, 182; 436/177, 178; 530/413, 417

[56] References Cited

U.S. PATENT DOCUMENTS

| | | | |
|---|---|---|---|
| 4,163,714 | 8/1979 | Gregor | 210/639 |
| 5,286,449 | 2/1994 | Kuroda et al. | 422/48 |
| 5,310,688 | 5/1994 | Zale et al. | 210/500.21 |
| 5,418,061 | 5/1995 | Parham et al. | 428/398 |
| 5,683,916 | 11/1997 | Goffe et al. | 210/500.23 |

FOREIGN PATENT DOCUMENTS

| | | |
|---|---|---|
| 0488095 | 6/1992 | European Pat. Off. |
| 9005018 | 5/1990 | WIPO |
| 9302777 | 2/1993 | WIPO |

OTHER PUBLICATIONS (C) WPI/Derwent; Kuraray Co. Ltd., Treatment of Liquied For Analytical Or Medical Use Using Porous Holloiw Fibre Through Which Immobilised Physiologically Active Substance Permeates, 9 pp; 8 May 1986.

*Primary Examiner*—John Kim
*Attorney, Agent, or Firm*—Thomas S. Borecki; Charles R. Mattenson; Robert M. Barrett

[57] ABSTRACT

The present invention provides an improved affinity membrane device and method for the effective removal of target molecules in plasma. The affinity membrane device is designed for use in an extracorporeal blood circuit and can be employed concurrently with other therapeutic processes for the purification of blood. The device of the present invention consists of hollow fiber membranes having specified dimensions and transfer properties, ligand immobilized to the pore surface of the hollow fibers, and a housing to encase the hollow fibers and allow appropriate entry and exit of the blood. In a preferred embodiment, specific immobilization chemistries are utilized to attach the ligands to the hollow fibers for optimal function.

8 Claims, 1 Drawing Sheet

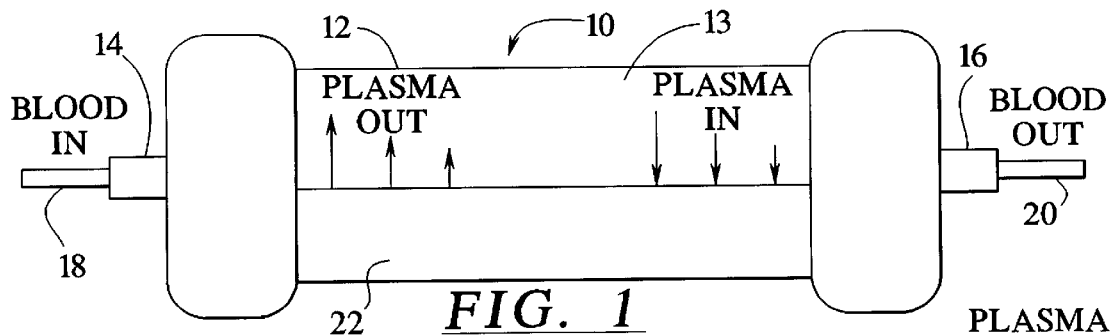
FIG. 1
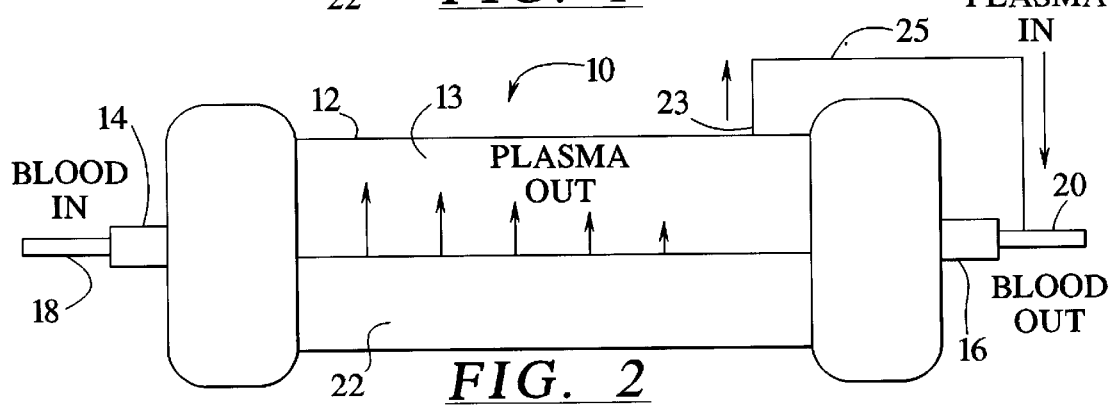
FIG. 2
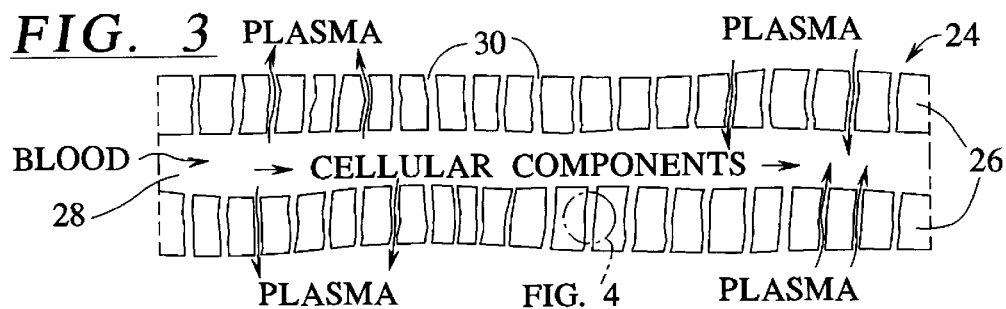
FIG. 3
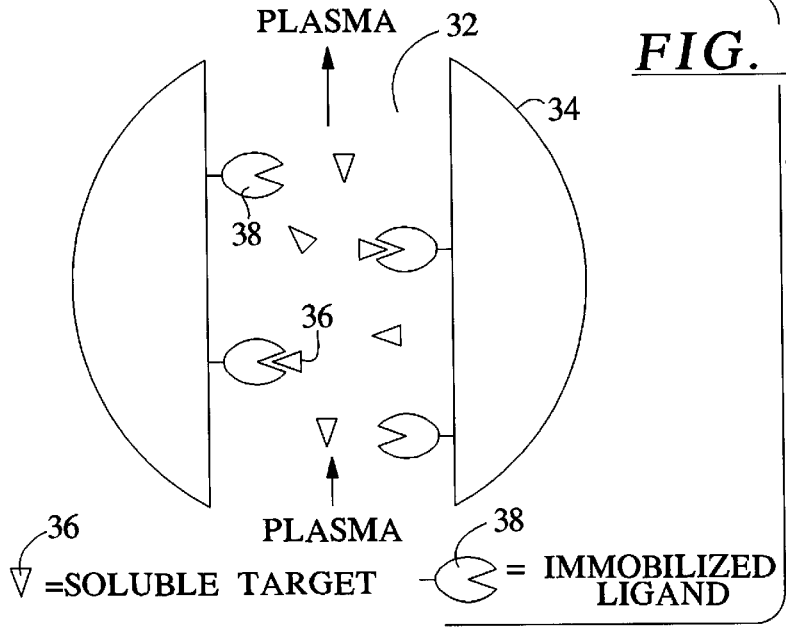
FIG. 4
▽ = SOLUBLE TARGET
⊂ = IMMOBILIZED LIGAND
FIG. 5

AFFINITY MEMBRANE SYSTEM AND METHOD OF USING SAME

This is a division of application Ser. No. 08/668,582, filed on Jun. 20, 1996.

BACKGROUND OF THE INVENTION

The present invention relates generally to therapeutic processes designed for the purification of blood. More specifically, the present invention relates to affinity membrane systems designed to remove specific solutes from blood.

Affinity separations rely on the highly specific binding between a molecule in solution and an immobilized ligand to achieve a high degree of purification. Conventionally, separations are performed on affinity columns packed with porous beads in which the ligand is immobilized. Such ligand is located deep in the pores of the porous beads. The affinity separations proceed by pumping the protein solution through the packed bed containing the porous beads.

These column systems, which are currently used for absorptive plasma treatment, are based on devices and adsorbance which, in many cases, have been adapted for other types of separation processes, such as industrial separation. Naturally, the goals driving the development of an industrial separation process may be quite different from those associated with a therapeutic procedure. This difference can result in an adopted technology which, while efficacious, is far from optimal. See Kessler, "Adsorptive Plasma Treatment: Optimization of Extracorporeal Devices and Systems," *Blood Purification*, Vol. 11, pp. 150–57 (1993) (hereinafter Kessler, "Adsorptive Plasma Treatment").

A variety of goals have been postulated for the design and optimization of extracorporeal systems for plasma treatment. One of the primary goals is to minimize the amount of costly ligand, usually an antibody, utilized to capture the target molecule. By minimizing ligand quantity, the cost per treatment can be reduced substantially. Another goal is to minimize system volume, which in turn minimizes the impact of the procedure on the patient. Such volume minimization can reduce both acute reactions and chronic effects such as protein loss. See Kessler, "Adsorptive Plasma Treatment," p. 150 (1993). From a marketing perspective, other desirable characteristics of an affinity device are that it be easily scaled up and manufactured, and that it require little ancillary hardware for operation.

As noted above, current therapeutic devices which are utilized to remove targeted molecules consist of columns packed with porous beads. A number of disadvantages exist with these devices. For instance, the capture rate in these devices is limited by slow intraparticle diffusion, especially for large target solutes, and high pressure drops with higher flow rates. See Suen & Etzel, "A Mathematical Analysis of Affinity Membrane Bioseparations," *Chemical Engineering Science*, Vol. 47, No. 6, pp. 1355–1364 (1992) (hereinafter Suen & Etzel, "Mathematical Analysis"). Such diffusion-limited adsorption leads to inefficient use of expensive ligand since significant amounts of ligand may be inaccessible to target solute.

Aside from the problems associated with diffusion-limited adsorption, other disadvantages also exist. In order to limit the size and cost of separation devices, two columns are usually employed, using one column for adsorption while target solute is eluted from the other. The use of two columns not only increases the cost of the process but also increases the treatment time needed to conduct the separation and solute removal. Moreover, the slow flow rates used to avoid excess pressure drop across the bed in such columns result in increased loading times.

Still further, the bioincompatibility of the substrate material in such columns necessitates the separation of plasma from the other cellular components of the blood prior to introduction of the plasma into the packed bed column. The blood is initially separated into cellular components and plasma components by a process known as plasmapheresis. Plasmapheresis may be performed by either filtration or centrifugation. Membrane plasmapheresis uses membranes with pore sizes greater than the size of plasma proteins but smaller than the cellular components of blood which allows the separation of the plasma. Centrifugation separates components on the basis of density in either a batch or continuous process. Next, the blood plasma is pumped through a packed column to remove targeted solutes, such as toxins. The treated plasma is then combined with the cellular components and returned to the patient. This multistep process is time consuming and utilizes large extracorporeal volumes. The process also requires a great deal of equipment and substantial handling of blood products, which leads to increased potential for infections.

In recent years, hollow fiber membranes have been proposed as an attractive alternative to porous beads as an affinity substrate. The large surface area present in the flow channels of the fiber wall eliminates the diffusional limitations imposed by adsorption associated with porous beads. Shifting the rate limiting step to the adsorption kinetics between target solute and membrane-bound ligand allows the use of greater flow rates and potentially more efficient use of ligand, as all ligand is accessible to bind target solute.

Attempts have been made to formulate affinity type systems to facilitate the removal of targeted solutes from bloods. For instance, Shettigar et al, U.S. Pat. No. 5,211,850, relates to a hollow fiber system in which sorbent beads are placed in a specially designed U-shaped device. In the device, plasma solutes are preferably filtered through the porous hollow fiber membrane into a plasma chamber where unwanted components are removed by adsorptive binding techniques. Plasma and unbound solutes then reenter the hollow fiber and are returned to the patient.

Parham et al, U.S. Pat. No. 5,258,149, relates to the removal of low density lipoprotein cholesterol complex from whole blood. The system set forth in Parham et al is directed to utilizing a microporous plasmapheresis membrane wherein an immobilized affinity agent is integral to the membrane. A blood pump is utilized to pump the whole blood into the affinity membrane. Another pump, namely a plasma pump, is then utilized to draw plasma through the channels of the microporous fibers and separate same from the cellular components of the blood.

SUMMARY OF THE INVENTION

The present invention provides an improved affinity membrane device for the removal of targeted solutes from blood. The inventors of the present invention have discovered that the fibers utilized in an affinity membrane device must be specifically designed for the device to perform adequately under the operating constraints of an extracorporeal device. A variety of interacting fiber characteristics, including the internal radius, length, pore size and wall thickness, must be considered when designing such an affinity membrane device. Likewise, carefully controlled operating conditions with respect to blood flow and fluid shear rate must be utilized in the extracorporeal blood circuit to prevent excessive volume changes within the patient or excessive damage to cellular components in the blood.

Prior to the present invention, the inventors believe that no one has investigated and determined how to successfully prepare an affinity membrane device that would be suitable in therapeutic applications. While hollow fiber membranes have been utilized in separation processes and flat sheet affinity membranes are available, many therapeutic applications present stringent operating requirements on a hollow fiber affinity system that have not been addressed in previous work. Pursuant to the present invention, an affinity membrane device is provided that can be utilized to treat a number of medical conditions characterized by excessive levels of a specific solute in blood.

The affinity membrane device of the present invention can be utilized for the selective removal of targeted molecules contained in plasma or blood. The simplified but effective affinity membrane device of the present invention has an elongated housing having an inlet port and an outlet port for entry and exit of blood therefrom. Additionally, the membrane device includes hollow fibers encased inside the housing. The hollow fibers have pores with suitable pore size for separating blood into plasma and its cellular components. The pores also have ligand immobilized on an interior surface of the pores; the ligand has an affinity for and, in an embodiment, binds the targeted molecule present in the plasma being transported into the pores of the hollow fibers. In another embodiment, the ligand may be an enzyme that can modify and release the targeted molecule. Notably, the cellular components of the blood do not enter into the pores of the hollow fibers; whereas, the plasma is transported into the pores by means of positive and reverse filtration in the absence of an external pump for generation of plasma flow across the hollow fibers.

In an embodiment, the pore sizes range from approximately 0.2 to 0.6 microns.

In an embodiment, the hollow fibers have wall thicknesses with adequate surface area for attachment of the ligands to allow for the sufficient binding of the targeted molecule. To this end, the wall thickness of the hollow fibers preferably range from approximately 300 to 3500 microns.

In an embodiment, the hollow fibers have internal diameters of approximately 70 to 140 microns.

The present invention also provides a method for the selective removal of targeted molecules present in plasma of blood. Initially, the method includes providing an affinity membrane device made pursuant to the present invention. Next, blood is pumped into the inlet port of the housing. The plasma of the blood is then transported into the pores of the hollow fibers by means of positive and reverse filtration while not allowing the cellular components to enter into the hollow fiber wall. The targeted molecules in the plasma are caused to come into close proximity with the ligands for a clinically significant period of time to allow for the binding or modifying of the targeted molecules. Lastly, in an embodiment, by means of positive and reverse filtration, the non-targeted molecules of the plasma are transported through the pores of the hollow fibers to reunite with the cellular components of the blood and exit the device through the outlet port. In another embodiment, the non-targeted molecules of the plasma are reunited with the cellular components via a plasma tubing by means of an existing pressure gradient.

Still further, the present invention provides a hollow fiber device having specified dimensions and transport properties.

The hollow fiber device contains a multitude of elongated hollow fibers. Each hollow fiber has a peripheral wall surrounding a lumen. The peripheral wall has a plurality of pores extending therethrough. The number and dimensional configurations of the pores are effective to separate blood into plasma and cellular components. The pores have ligand bound to their internal surface. The peripheral wall has a wall thickness (a sufficient pore length dimension) such that adequate surface area is provided for the attachment of the ligand to ensure that the ligand captures an adequate quantity of targeted molecule.

An advantage of the present invention is that it obviates the need for a distinct plasmapheresis step through judicious design of the hollow fiber membrane. As noted previously, prior embodiments have required contact with plasma instead of whole blood and consequently needed plasmapheresis concurrent with the use of the separation membrane.

Another advantage of the present invention is that the contacting surfaces of the membrane device are more biocompatible than affinity columns previously employed in the field. Improved biocompatibility will result in lower complement activation during treatment.

Still further, an advantage of the present invention is that it utilizes an immobilization chemistry that allows for attachment of a wide variety of ligands using a simplified, streamlined process. The process represents significant improvements over previous attempts to prepare affinity membranes. The attachment chemistry of the present invention can be readily utilized for the attachment of a variety of ligands, as opposed to a single ligand.

Another advantage of the present invention is that one of the immobilization chemistries utilized demonstrates greater ligand utilization over previous attempts when target solute is much larger than the immobilized ligand.

Still further, an advantage of the present invention is that it provides significant cost improvements over available affinity columns. Cost reductions are realized in ease of manufacture, reduction in ligand requirements, and simplicity of equipment for use.

Yet another advantage of the present invention is that it is significantly easier to use than a comparable affinity column. The invention requires less supporting equipment and less oversight by health-care professionals.

Another advantage of the present invention is that it possesses improved mass transport properties that can result in shorter treatment time, greater utilization of costly ligand, or a combination of both.

Moreover, an advantage of the present invention is that it provides a membrane device that is simplified yet more efficient than prior membrane devices proposed in the art. In this regard, the membrane device of the present invention uniquely does not require the use of an external pump for generating plasma flow across the hollow fibers of the device. Moreover, pursuant to the present invention, an elongated housing is utilized to encase the hollow fibers and promote the positive and reverse filtration within the device. Unlike prior systems, the inventors of the present invention have discovered that a U-shaped design is not required to promote positive and reverse filtration.

Additional features and advantages of the present invention are described in, and will be apparent from, the detailed description of the presently preferred embodiments as well as the drawings.

BRIEF DESCRIPTION OF THE DRAWINGS

FIG. 1 is a plan view of one embodiment of the affinity membrane device of the present invention.

FIG. 2 is a plan view of another embodiment of the affinity membrane device of the present invention.

FIG. 3 is a schematic magnified representation of a single hollow fiber illustrating the flow of plasma through the fiber wall by means of positive and reverse filtration that occurs within the interior cavity of the affinity device.

FIG. 4 is a schematic magnified representation of a single fiber wall of a hollow fiber illustrating the flow of the plasma through the pore in the fiber wall and the binding of targeted molecules onto immobilized ligands.

FIG. 5 generally illustrates the biotin-avidin immobilization scheme of the present invention.

DETAILED DESCRIPTION OF THE PRESENTLY PREFERRED EMBODIMENTS

The present invention provides an affinity membrane device designed to remove specific, deleterious solutes (target solutes) from blood. The affinity membrane device is designed for use in an extracorporeal blood circuit and can be employed concurrently with other therapeutic processes for the purification of blood, such as hemodialysis. The device of the present invention consists of hollow fiber membranes having specified dimensions and transport properties, ligands immobilized to the pore surface of the membranes, and a housing to encase the hollow fibers and allow appropriate entry and exit of blood and filtrate. In a preferred embodiment, the ligand is attached to the membrane with a specific immobilization chemistry for optimal function.

In use, the immobilized ligand binds or modifies a specific target solute, thereby effecting removal of such solute from blood passing through the lumen of the hollow fibers. The positioning of the ligands as well as the unique immobilization chemistry utilized in the present invention results in an affinity membrane device with improved retention of ligand activity, system flexibility, standardization of membrane manufacturing, and a potential for overall increased efficiency. Notably, the affinity membrane device of the present invention can be utilized to treat a number of medical conditions characterized by excessive levels of a specific solute in blood.

FIG. 1 illustrates an embodiment of the affinity membrane device of the present invention. The affinity membrane device can be utilized for the selective removal of a variety of targeted solutes from blood. For example, the device could be utilized to remove low density lipoprotein ("LDL"), beta 2-microglobulin, immunoglobulins, autoantibodies and the like.

The membrane device 10 has an elongated housing 12 defining an interior cavity 13. The inlet port 14 is connected to an inlet conduit 18 and allows the entry of blood into the affinity membrane device 10. After the affinity membrane device 10 acts on the blood, the treated blood is then exited from the system through outlet port 16 connected to outlet conduit 20.

The membrane device 10 also includes a multitude of hollow fiber membranes 22, actually a bundle of membranes that make up a hollow fiber membrane filter, encased in the interior cavity 13 of the elongated housing 12. As detailed further below, the hollow fiber membranes 22 have pores with suitable pore sizes for separating the blood that passes through the membranes 22 into plasma and its cellular components. The plasma separates from the cellular components of the blood and, as graphically illustrated, flows out through the pores in the walls of the hollow fiber membranes 22.

Due to the transmembrane pressure within the membrane device 10, the plasma ultimately flows back through the pores in the walls of the hollow fiber membranes 22 and reunites with the cellular components of the blood. In this regard, due to the axial pressure drop within the fibers, the transmembrane pressure varies along the length of the device 10. Near the inlet port 14, transmembrane pressure is positive, causing plasma to flow from lumen to the shell space of the elongated housing 12. Near the outlet port 16, transmembrane pressure is negative, thereby causing plasma to then flow from the shell space back to the lumen.

An alternative embodiment of the present invention that also allows for the effective transport of the plasma through the pores is illustrated in FIG. 2. FIG. 2, where the features similar to FIG. 1 are identified by like numbers, illustrates an embodiment of the present invention utilizing a plasma outlet port 23. Unlike the embodiment depicted in FIG. 1, the plasma in this device exits out through outlet port 23. However, similar to the embodiment of FIG. 1, the axial pressure gradient within the affinity membrane device creates the filtrate (plasma) flow across the hollow fibers. Due to the design of the device 10, the transmembrane pressure is positive throughout the device. The outlet port 23 is connected to the outlet conduit 20 via a plasma conduit 25, thereby allowing the non-targeted molecules of the plasma to be reunited with the cellular components of the blood by means of an existing pressure gradient.

FIGS. 3 and 4 specifically illustrate the principle of plasma separation and solute removal as utilized in the present invention. FIG. 3 illustrates a single hollow fiber 24 of the affinity device. It specifically illustrates the separation of plasma from the cellular components of the blood in the affinity membrane device of the present invention.

The hollow fiber 24, only one of the bundle being depicted here, has a central lumen 28. Whole blood, which was removed from a patient, passes from the inlet port of the device through this lumen 28 to the outlet port of the device. The wall 26 of the fiber 24 has a series of openings or pores 30 through which plasma, toxins, drugs or other solutes having diameters smaller than the pores 30 can pass into the wall 26 of the fiber 24. Other cellular components, such as red blood cells, white blood cells and platelets are of a size that they do not pass through the pores 30 and remain in the lumen 28 of the fiber 24.

The plasma components flow into and out of the hollow fiber 24 by means of positive and reverse filtration. Initially, as the blood to be treated is transported into the membrane device, the pressure of the blood inside of the hollow fiber 24 causes plasma to pass from the lumen 28 by convection towards the wall of the interior cavity or, in other words, towards the shell of the elongated housing. Then, near the outlet port of the device, the pressure inside the hollow fiber membrane 24 is lower than the pressure of the plasma outside of the fiber (that at the wall of the interior cavity). As a result, the plasma then flows back into the lumen 28.

The plasma that flows back through the wall 26 of the fiber 24 has been treated or modified with the ligands immobilized to the surface of the pores 30 of the fiber 24. Therefore, the treated plasma is safely reunited with the cellular components in the lumen and exits out through the outlet port. A patient's blood is allowed to recirculate through the device until the concentration of the target solute is sufficiently reduced.

Ligands bound on the surface of pores 30 act on the plasma to remove targeted solutes from the plasma or, in another embodiment, to modify such targeted solutes. The manner in which the ligand is immobilized to the pore surface of the affinity membrane depends on the type of ligand (e.g. antibody, antigen) as well as the membrane material being utilized. A selective immobilization scheme should be utilized such that the greatest amount of target solute can be captured by the membrane with a minimum amount of ligand. As those skilled in the art can appreciate, some general concerns that should be considered are the use of gentle reaction conditions for the immobilization, the bond stability to physiologic and elution conditions, and the site directed chemical methods to maintain integrity of an active site.

Pursuant to the present invention, a variety of immobilization techniques could be utilized to attach the ligands to the surface of the pores in the hollow fiber membranes. In addition to the improved immobilization methods detailed in the present invention, immobilization methods for activated membranes could be modified for use in the affinity device of the present invention. For example, some activated membranes are commercially available for direct immobilization of protein ligands. Notably, however, all of these membranes are available in flat sheet form only. Examples include: Immobilon™ (available from AV Millipore Corporation, Bedford, Mass.); Imunodyne™ (available from Pall Biosupport Corporation, Glen Cove, N.Y.); and UltraBind™ (available from Gelman Sciences, Ann Arbor, Mich.).

As set forth in more detail below, the present invention sets forth improved immobilization techniques that provide significant advantages over prior procedures. In one preferred embodiment, an avidin/biotin complex is utilized for immobilization of the ligand to the pore surface. Alternatively, a polyethylene glycol immobilization technique can be utilized either independently or in conjunction with an avidin/biotin complex.

Unlike other systems that have utilized sorbent located in a plasma chamber, the present invention uniquely utilizes ligands immobilized directly on the surface of the pores 30 to remove targeted solutes from the plasma. The circled portion in FIG. 3 generally depicts where the ligands are immobilized to the surface of the pores 30. This procedure not only removes the need for a sorbent material located in the external plasma chamber, it increases the efficiency of the solute removal process as well as decreases the treatment time. With ligands present on the pores through which the plasma and plasma components are being directly transported, an increased probability exists that ligands will interact with the targeted solutes and thereby result in a greater utilization of the costly ligands.

The principle of solute removal utilized in the present invention is illustrated in FIG. 4. FIG. 4 is a magnified representation of a single pore 32 in the fiber wall 34 of a hollow fiber membrane. When the plasma passes through the wall 34 of the fiber membrane, specific targeted molecules 36 come in contact with ligand 38 immobilized on the surface of the pore 32. Effectively, the ligand 38 binds the targeted solute 36 such that the targeted solute 36 is removed from the plasma. The plasma is allowed to pass through the fiber wall 34 for a clinically significant amount of time to remove substantially all targeted solute 36 from the plasma.

The hollow fiber membrane of the present invention is advantageously made of blood compatible material which results in lower complement activation during treatment. Suitable fiber materials are cellulose triacetate, polysulfone, polyacrylonitrile, ethylene/vinyl alcohol copolymer, polymethylmethacrylate, polyamide, polypropylene, cellulose acetate, regenerated cellulose, polycarbonate, polyethylene, polyvinylalcohol, polyvinylchloride and the like. The hollow fibers must have a suitable pore size to allow the passage of plasma components, including targeted solutes, through the walls of the hollow fibers. At the same time, such pore size must also be able to prevent blood cells and platelets from entering into the pores of the walls. Suitable pore sizes (diameters) in the hollow fibers can range from approximately 0.2 to 0.6 microns.

Pursuant to the present invention, an affinity membrane device is provided that contains hollow fiber membranes having specified dimensions and transport properties. As noted above, a variety of factors must be considered in designing a hollow fiber device that will be suitable for use in therapeutic applications. The inventors of the present invention have discovered that the fibers utilized in an affinity membrane device must be specifically designed for the device to perform adequately under the operating constraints of an extracorporeal device. The interacting fiber characteristics, including the internal radius, length, pore size and wall thickness, must be evaluated in order to determine suitable hollow fiber membranes.

The inventors determined the suitable dimensions for a hollow fiber membrane device based on computer modeling. A computer model was developed to describe the performance of the affinity membrane device. In this regard, the computer model solved certain conservation equations in finite-difference form for radial and longitudinal segments of blood within the hollow fiber membranes. Unlike other proposed systems, the inventors have determined how the various interacting characteristics of hollow fibers must be formulated to produce a suitable hollow fiber membrane device.

The dimensions of a hollow fiber affinity membrane device are to a great extent determined by the amount of target solute which must be removed from the patient. Design of a device to satisfy these criteria results in a membrane with dimensions (length, inner radius, fiber wall thickness) which are uniquely suited to therapy with affinity membrane devices. While membranes used for affinity-based therapy also effect the separation of plasma from cellular components of blood, their primary function is to participate in the removal of target substances by providing a substrate of maximal surface area onto which ligands can be bound. This function greatly determines the optimal dimensions of such membranes and distinguishes their design from that of membranes designed purely for separation purposes.

Typically, membranes are used to achieve separation of target substances from a solution on the basis of their molecular size. In order to eliminate the resistance to mass transfer imposed by the membrane, these membranes are generally designed to be as thin as possible (as thin as 8 microns for dialysis membranes and up to several hundred microns for ultrafiltration membranes).

On the contrary, thicker membrane walls are advantageous for membranes in affinity devices, as the membrane itself provides the substrate for the attachment of ligands which will bind target solutes. Since the membrane area available for the attachment of ligands is a function of the fiber internal radius, thickness and length, providing adequate surface area for the immobilization of ligands in the device by increasing the membrane wall thickness is important. Such increase in wall thickness will allow the maximum binding or modifying of the target solute while minimizing the volume of the blood compartment of the device. In terms of the association kinetics between the target solute and ligand for any given filtrate flow rate (depicted by the arrows in FIG. 3), thick membranes provide maximum residence times for the target solute in the pores or "spongy matrix" of the membrane. As a result, this increases the likelihood that the target will contact and be captured by immobilized ligand.

The dimensions of a hollow fiber affinity membrane device are also determined by the filtrate flux required to effect therapeutic changes in plasma concentration. The specific filtrate flux required for a given therapy is determined by the volume of distribution and the plasma concentration of the target solute, and the treatment time for the therapy. The relationship for solute flux through a membrane in which the filtrate flux is governed by concentration polarization of red cells at the membrane surface has been described previously. See Zydney et al, "A concentration polarization model for the filtrate flux in cross-flow microfiltration of particulate suspensions," *Chemical Engineering Communication*, Vol. 47, pp. 1–21 (1986)(hereinafter Zydney et al, "Concentration Polarization Model"). The flux is dependent on the shear rate of blood through the device, the length of the device and the degree of polarization of cells.

A hollow fiber affinity membrane device that has been designed to provide sufficient target capacity and adequate filtrate flux for clinical effectiveness must simultaneously satisfy a number of system constraints based on physical considerations.

In a hollow fiber membrane device, the shear rate for the flowing fluid must not be great enough to damage components of the flowing fluid, notably red blood cells which are sensitive to shear effects. Since the shear rate in a hollow fiber device is determined by the blood flow rate, the fiber internal radius, and the number of fibers, these parameters may be limited by the constraint on the system shear rate.

Blood flowing through the lumen in a hollow fiber membrane device experiences a decrease in pressure along the axis of the lumen. In practice, the magnitude of this axial pressure drop is limited due to material and equipment considerations. This constraint may limit acceptable values for fiber internal radius, fiber length, and number of fibers.

In a hollow fiber membrane device, filtrate flowing through the pores in the wall of the membrane experiences a decrease in pressure along the axis of the pore. In practice, the magnitude of this transmembrane pressure drop is limited due to material and equipment considerations, and this constraint may limit acceptable values for the fiber wall thickness.

Still further, convection-dominated transport is preferred over diffusion-dominated transport in a hollow fiber membrane device. Convective transport facilitates delivery of target solute uniformly throughout the spongy matrix of the membrane in such a manner as to optimize the interaction between unoccupied binding sites and target solute. Notably, a design of affinity membranes in which transport is dominated by convection results in a more efficient device (i.e., the therapy may be conducted in the shortest possible time). The relative contribution of convection and diffusion can be expressed by the system Peclet number, for which values greater than 40 indicate that transport is dominated by convection. See Suen & Etzel, "Mathematical Analysis."

Moreover, in a hollow fiber affinity membrane device, manufacturing considerations may limit the physical size of the device and subsequently may place constraints on certain parameters. For example, parameters such as fiber wall thickness, fiber internal radius, fiber length, and number of fibers may be constrained.

In a hollow fiber membrane device used for extracorporeal therapy, total extracorporeal blood volume will be strictly limited for patient safety. Consequently, fiber wall thickness, fiber internal radius, fiber length, and number of fibers may be limited by this constraint.

Aside from designing an optimal fiber membrane, the binding chemistry must be carefully chosen and optimized (as described elsewhere) to obtain the highest binding capacity possible. This will result in the most efficient use of the membrane and ligands.

If the device is configured as in FIG. 1, sufficient length of the fibers, in addition to that needed for adequate capture of target solute in the forward direction (plasma from lumen to shell-side), must be included so that the plasma can return to the lumen of the fibers and exit the device. The length of fiber which must be added is dependent upon the permeability and thickness of the membrane polymer used.

For a given set of therapy requirements, it is possible that the design parameters of a single device operating in single pass mode cannot satisfy the therapy requirements subject to the system constraints outlined above. In such cases, a process of regenerating the membrane device by periodically eluting the target solute during therapy may allow the device to satisfy therapy requirements within the system constraints. In order to avoid interrupting the therapy during regeneration, two devices may be employed during treatment, so that one can bind or modify solute while the other is undergoing regeneration.

By way of example and not limitation, the inventors calculated appropriate hollow fiber dimensions for various target solutes using the following equations which represent the requirements and constraints described above.

EXAMPLE OF SUITABLE DIMENSIONS

The quantity of target solute to be removed is governed by the therapeutic requirement:

quantity to be removed=$V(C_c-C_f)$ where: V=volume of distribution of target solute
$C_c$=initial concentration of target solute
$C_f$=final concentration of target solute The total capacity of the affinity membrane device is equal to the specific capacity ($C_p$) times the membrane volume:

total capacity=$[(r+d)^2-r^2]\pi LNC_p$ where: r=radius of hollow fiber
d=thickness of hollow fiber wall
L=length of hollow fiber
N=number of hollow fibers The first requirement for affinity membrane device dimensions is that the total capacity of the affinity membrane device must be greater than the quantity to be removed:

$$[(r+d)^2-r^2]\pi LNC_p > V(C_o-C_f) \tag{1}$$

The volumetric flowrate ($Q_f$) required to achieve the final target concentration within a treatment time (t) is calculated from a mass balance on the target solute.

Assuming complete solute adsorption in a single pass (i.e. a perfectly designed membrane), this requirement is given by:

$$Q_f = \frac{-V}{t} \ln \frac{C_f}{C_o} \tag{2}$$

Assuming that flow through the membrane is concentration polarization limited, the desired filtrate flowrate can be predicted from the following relationship (See Zydney et al, "Concentration Polarization Model."):

$$\frac{Q_f}{Q_b} = 1 - \frac{H}{C_w} e \left[ \ln \frac{0.95}{H} e^{-B} \right] \quad (3a)$$

$$\text{Where: } B = 2.0 \times 10^{-5} \left[ \frac{L}{r^3} \right]^{2/3} \quad (3b)$$

and: $Q_b$=Inlet blood flow rate

H=Inlet blood hematocrit (Units of B are consistent with L and r expressed in cm.)

The specific capacity ($C_p$) for a given target solute is maximized by appropriate selection of the ligand which binds the target, the membrane material, and the chemistry employed for attaching the ligand to the membrane.

The remaining design parameters which appear in equations (1) through (3) are the device dimensions r, d and L and the number of fibers (N). As previously discussed, these design parameters are subject to a number of constraints.

One constraint on r is the maximum permissible wall shear rate, given by:

$$\text{maximum wall shear rate} = \frac{4Q_b}{\pi r^3 N} < 2500 \text{ s}^{-1} \quad (4)$$

Another constraint on r is the maximum permissible axial pressure drop:

$$\text{maximum pressure drop} = \frac{8\mu_b L Q_b}{\pi r^4} < 1000 \text{ mmHg} \quad (5)$$

where $\mu_p$=blood visocity

L is constrained by the above-mentioned pressure drop limitation as well as the following practical constraint on the overall physical size of the device:

$$N\pi(r+d)^2 < 78.5 \text{ cm}^2 \quad (6)$$

The thickness (d) is constrained by the above constraint as well as the Peclet number constraint and the transmembrane pressure constraint:

$$vd/D < 40 \quad (7)$$

Where D is the diffusivity of the target solute and the filtrate velocity v is given by:

$$v = \frac{Q_f}{2\pi r N L} \quad (8)$$

The transmembrane pressure drop can be determined using the Blade-Kozeny equation for packed beds. (See Bird, Stewart, Lightfoot, "Transport Phenomena," (1960)). This equation is as follows:

$$\Delta P_{transmembrane} = \frac{150 v d\mu_f (1 - \epsilon)^2}{D_p^2 \epsilon^2} \quad (9)$$

Where: $\mu_f$=the filtrate viscosity $D_p$=the pore diameter of the membrane=0.25 microns $\epsilon$=membrane porosity=0.7

Using the above equations for the design requirements and constraints, the inventors determined that the hollow fibers of an affinity membrane device should have wall thicknesses of approximately 300–3500 microns and internal diameters of approximately 70–140 microns.

In addition to determining the optimal design process for design of suitable hollow fiber membranes, the inventors of the present invention have also determined an improved method of attaching ligands to the surface of pores in an affinity membrane device. The improved method results in increased efficiency of the device, greater utilization of the ligands, membrane standardization, simplicity, marketing flexibility and system flexibility. Membrane standardization refers to the ability to standardize the immobilization process for use with a wide variety of available ligands.

As noted above, the prior development of solute removal devices, either in the form of membranes or bead columns, has focused on the removal of a single target solute. With such focus, developers generally optimized their removal system for a specific ligand-target pair of interest and ignored questions of applicability to other ligand-target pairs. Immobilization chemistries for coupling ligands to a support matrix were very specific and were not readily transferable for use with other ligands.

Pursuant to the present invention, in an embodiment, an immobilization procedure is utilized that incorporates avidin and biotin. A specific immobilization chemistry is employed to couple avidin to the membrane surface. This process can be standardized for use with a wide number of available ligands. System flexibility is retained in the attachment chemistry by linking biotin molecules to the ligand.

The unique avidin/biotin immobilization chemistry of the present invention proceeds as follows. One or more molecules of biotin are covalently attached to a ligand. Avidin is covalently attached to the membrane pore surface. The respective attachment of the avidin and the biotin can be conducted using known techniques in the art. Then, the biotinylated ligand is caused to react with a membrane containing immobilized avidin, thereby resulting in the immobilization of the biotinylated ligand to the membrane.

FIG. 5 graphically illustrates the use of an avidin/biotin complex to immobilize ligand and capture target solute. Biotinlyated ligand 40 is bound to the avidin 42 that is immobilized on the pore surface 44 of the membrane. As illustrated there, the biotinlyated ligand 40 then is free to capture a targeted molecule 46 from a plasma solution.

Notably, the resulting avidin-biotin complex exhibits significant stability. The interaction between avidin and biotin is the strongest known noncovalent, biological interaction ($K_a=10^{15}M^{-1}$) between protein and ligand. Moreover, the bond formation between biotin and avidin is very rapid and, once formed, is unaffected by wide extremes of pH, temperature, organic solvents and other denaturing agents. For instance, the biotin-avidin complex can withstand temperatures up to 80° C., and pH ranging between 2 and 13.

With respect to the attachment of biotin to a ligand, many biotin derivatives, which are commercially available, allow biotin to be covalently coupled to a ligand through a number of functional groups. For instance, biotin can be coupled to specific sites within a protein ligand, including specific amino acid residues containing a terminal amine (lysine), an imidazole group (histidine), a phenol group (tyrosine) or a sulfhydryl group (cysteine). In addition, biotin derivatives are available for coupling to carbohydrate groups present in either sugars or mammalian proteins. Such chemistry is effective for coupling biotin to, for example, immunoglobulin G (IgG) at a site which does not interfere with antigenic binding. This chemical flexibility provides a number of potential methods to attach biotin to a ligand and increases the chances that a suitable method will be available for ligands of interest.

The attachment of avidin, due to its molecular structure, to a membrane surface insures the efficient use of ligand. Avidin is a tetrameric protein and each molecule is capable of binding up to four molecules of biotin with equal affinity. This multiple functionality present in each avidin molecule insures that immobilized avidin retains some ability to bind biotin. Generally, nonspecific immobilization of proteins to solid matrices results in the inactivation of some portion of the protein on the surface either through reaction with the protein's active site or stearic shielding of the active site from target molecules in solution. Given the symmetry of the avidin molecule, immobilization to a solid surface will inactivate one or more potential biotin binding sites; however, it also guarantees that one or more binding sites will remain active and free to bind biotin or a biotinlyated ligand.

The final step toward the preparation of an active affinity membrane is the formation of the avidin-biotin complex. Preferably, this formation occurs by reacting a membrane containing immobilized avidin with a solution containing biotinylated ligand. This reaction occurs rapidly and can be conducted under mild conditions, such as in dialysate buffer at room temperature. Uniquely, since this reaction step is simple and straightforward, the inventors believe it is conceivable that an end user could activate an avidin membrane with the biotinylated ligand of choice.

The ability to allow end users to activate the membranes of an affinity device provides significant advantages over prior systems. Aside from the simplicity of the process, this aspect of the present invention provides increased system flexibility and membrane standardization, which further results in marketing flexibility. Pursuant to the present invention, the end user could be supplied with a single avidin membrane and a variety of solutions containing different biotinylated ligands. Then, depending on the condition to be treated, the user can activate the avidin membrane with the appropriate ligand and flush away excess ligand with saline or dialysate.

In addition to its role in the chemistry of immobilization, avidin also acts as a hydrophilic spacer between the membrane surface and the immobilized ligand. The use of a molecular spacer to physically separate the solid matrix surface from the active site of the ligand is known in immobilization chemistry. In this regard, molecular spacers have been relatively short aliphatic chains (4 to 10 carbon atoms in length), which may be adequate to facilitate surface interactions or interactions involving small ligands or target solutes. However, these short chains are relatively ineffective when the interaction involves one or more macromolecules. On the other hand, the use of longer aliphatic chains undesirably alters the hydrophobicity of the membrane surface. Thus, utilizing avidin in the present invention not only provides an improved immobilization procedure, it also has a dual role as a spacer molecule that does not exhibit the disadvantages of prior spacers.

In most instances avidin will serve as a suitable spacer molecule, however, a potential disadvantage of using avidin is the density limitation imposed by avidin when both ligand and target are relatively small. In this situation, a saturated monolayer of avidin can be the limiting factor regarding the specific capacity of the membrane for binding solute. However, in most situations, either the ligand, its target molecule, or both are sufficiently large such that avidin's saturation limit is not the limiting factor to membrane capacity.

In the present invention, the inventors disclose a second improved method of attaching ligands to the surface of pores in an affinity membrane device. The improved method results in increased efficiency of the device, greater utilization of the ligands, and enhanced device capacity.

As noted above, the use of a molecular spacer facilitates molecular interactions between immobilized ligands and target solutes. Relatively short aliphatic chains (4 to 10 carbon atoms in length) are ineffective for interactions involving one or more macromolecules, but longer aliphatic chains undesirably alters the hydrophobicity of the membrane surface.

Pursuant to the present invention, in an embodiment, an immobilization procedure is utilized that incorporates polyethylene glycol (PEG, also known as polyethylene oxide). Polyethylene glycol of a suitable chain length, generally between 50 and 250 carbon atoms, is covalently immobilized to the membrane surface using a specific immobilization chemistry. After blocking remaining active sites, the ligand of interest is subsequently covalently coupled to the polyethylene glycol using a suitable chemistry. The unique advantages of polyethylene glycol as a molecular spacer include its hydrophilic nature and its biological inertness, both of which are quite beneficial in a device that contacts blood or plasma.

By way of example and not limitation, a simple method of immobilization of a heterofunctional PEG will now be described. The heterofunctional PEG can be obtained from a commercial vendor and has an amino terminus at one end and a carboxy terminus at the other. The heterofunctional PEG can be immobilized to the surface through its amino terminus using any one of a number of suitable immobilization chemistries which react with amino groups. As described above, these methods include those which utilize cyanogen bromide, N,N'-carbonyl diimidazole, and the like. After blocking of remaining reactive groups, the ligand of interest is covalently coupled to the carboxy terminus of the heterofunctional PEG using a suitable chemistry. One such reagent that facilitates the formation of amide bonds between a carboxyl group and an amine is 1-ethyl-3-(3-dimethylaminopropyl) carbodiimide.

The immobilization method using PEG has several advantages. First, the use of an extremely long molecular tether reduces steric interference at the surface and allows multiple layering of large macromolecules at the surface. In our experience with the avidin-biotin chemistry, for example, the presence of avidin projected the antibody-LDL interaction away from the membrane surface, but the overall capacity of the membrane was still limited by the available surface area on which LDL particles was bound. By extending long, flexible molecular chains from the membrane surface, the antibody was projected away from the membrane in such a way that may allow stacking of macromolecular targets. Neighboring chains may be of the same length, but by extending to varying degrees, a partially coiled chain bound to LDL may not interfere with LDL bound to a nearby chain which is fully extended.

While avidin also projects the antibody away from the membrane surface, a long, flexible spacer may more effectively project the antibody into the flowing liquid and enhance the kinetics of binding as well as the capacity.

Notably, while the PEG approach appears to possess many advantages, the chemical approach using PEG inherently may not have the chemical flexibility of the avidin-biotin scheme. As such, use of both PEG and an avidin-biotin complex together may be beneficial. In such an approach, avidin would be coupled to PEG which has been immobilized to the membrane surface. The avidin-biotin chemistry is then utilized as described above for ligand immobilization.

By way of example and not limitation, experimental results demonstrating some exemplary immobilization techniques will now be given. Notably, these examples illustrate various immobilizations performed on flat sheet membranes as opposed to hollow fiber membranes. These examples are being incorporated herein to demonstrate the improved immobilization schemes developed pursuant to the present invention. The following examples differ primarily in the material employed in the attachment chemistry: (1) avidin; (2) streptavidin; and (3) polyethylene glycol.

EXPERIMENTAL EXAMPLE 1

Sheep immunoglobulin G (IgG) directed against human apolipoprotein B (apoB) and isolated by affinity chromatography was oxidized with sodium metaperiodate (Sigma Chemical Co., St. Louis, Mo.). The reaction was quenched with glycerol, and the reactants separated from oxidized IgG by gel permeation chromatography. Oxidized IgG was biotinylated by reaction with biotin-LC-hydrazide (Pierce, Rockford, Ill.).

Avidin (Pierce) was immobilized to Immobilon AV membranes (Millipore) following the diffusional immobilization procedure in the manufacturer's instructions. Unreacted sites were capped with nonfat dry milk solution (1% w/w). Membranes containing immobilized avidin were immersed in a solution containing biotinylated IgG. The amount of IgG immobilized to the membrane was determined from the change in solution absorbance at 280 nanometers. The density of IgG was 143 $\mu$g per ml membrane volume.

Static membrane capacity was determined by incubation of the membranes in a solution of human plasma containing an excess of apoB. After extensive rinsing with buffer (phosphate buffered saline, pH 7.4), apoB was eluted from the membrane with 0.04M citrate buffer at pH 2.9. The amount of apoB present in the elution buffer was determined by a total protein assay (commercially available from BioRad).

The capacity of the resulting membrane was 31 $\mu$g apoB per ml membrane volume.

EXPERIMENTAL EXAMPLE 2

Preparation of oxidized IgG was as described in Example 1. Streptavidin (Pierce) was immobilized to Immmobilon AV membranes (Millipore Corporation, Bedford, Mass.) following the diffusional immobilization procedure in the manufacturer's instructions. Unreacted sites were capped with nonfat dry milk solution (1% w/w). Membranes containing immobilized streptavidin were immersed in a solution containing biotinylated IgG. The amount of IgG immobilized to the membrane was determined from the change in solution absorbance at 280 nanometers. The density of IgG was 1.39 mg per ml membrane volume.

Determination of static membrane capacity was performed as described in Example 1. The capacity of the resulting membrane was 30 $\mu$g apoB per ml membrane volume.

EXPERIMENTAL EXAMPLE 3

Preparation of oxidized IgG was as described in Example 1. Heterofunctional poly(ethylene glycol) ($NH_2$—PEG—COOH available from Shearwater Polymers, Huntsville, Ala.) was immobilized to Immobilon AV membranes following the dot immobilization procedure in the manufacturer's instructions. Unreacted sites were capped with ethanolamine (7% v/v). The immobilized poly(ethylene glycol) ("PEG") was reacted with adipic dihydrazide in the presence of 1-ethyl-3(3-dimethylaminopropyl) carbodiimide ("EDC") to create a functional site for attachment of oxidized IgG. Oxidized IgG was coupled to the PEG-hydrazide spacer, and the resulting Schiff base was reduced with sodium cyanoborohydride. The membranes were rinsed with distilled water and 1M NaCl solution prior to use.

Dynamic membrane capacity was determined by flowing a solution of human plasma through a membrane disc holder (available from Amicon) containing a stack of membrane discs. The volume of human plasma supplied to the membrane discs contained an excess of apoB. The number of membrane discs in the stack ranged from 5 to 20. The amount of apoB bound to the membrane was determined from the difference in plasma apoB concentration between the sample effluent from the holder and the initial sample. The concentration of apoB in plasma was determined with a commercial assay kit (available from Boehringer Mannheim Corporation, Indianapolis, Ind.).

The capacity of the resulting membranes ranged from 0.39 to 2.03 mg apoB per ml of membrane volume.

The present invention also provides a method for treating certain medical conditions characterized by excessive levels of a specific solute in blood. As noted previously, the affinity membrane device of the present invention is designed for use in an extracorporeal blood circuit and can be employed concurrently with other therapeutic processes for the purification of blood, such as hemodialysis. The immunoadsorptive therapy available by using the present invention can serve as a beneficial treatment scheme for certain medical conditions. Specifically, the present invention may be utilized to treat medical conditions that are associated with the presence of a specific molecular entity in plasma for which removal remedies the condition on either a temporary or permanent basis. In addition to the identification of a molecular target in plasma, the use of the present invention for the treatment of such conditions is premised on the ability to identify suitable ligand capable of binding and removing such molecular target from plasma.

By way of example and not limitation, examples of medical conditions that may be treated pursuant to the present invention include hypercholesterolemia, transplant rejections associated with IgG or IgM, Goodpasture's syndrome, systemic vasculitis, and systemic lupus erythematosus. Each of these conditions is characterized by containing excess levels of a specific solute in blood. For example, patients suffering familial hypercholesterolemia are characterized as possessing increased levels of low density lipoprotein (LDL), the removal of which acts as an effective treatment for the medical condition.

Pursuant to the present invention, the affinity membrane device may not only be utilized to remove target solute from a patient to be treated, but it also may be employed concurrently with other separation processes (e.g. hemodialysis). In this regard, certain therapeutic applications can advantageously be utilized for patients who are currently receiving hemodialysis therapy for End Stage Renal Disease (ESRD). Such therapeutic applications include, for example, the extracorporeal removal of LDL, beta 2-microglobulin, and IgG for allogenic transplant recipients. These patients are ideally suited for extracorporeal therapy since many already undergo extracorporeal hemodialysis therapy for three to four hours three times a week. Moreover, many of these patients have already undergone surgery to create an access to their vascular system that will allow use of high blood flow rates (>200 ml/min).

The ability to employ the present invention concurrently with a hemodialysis procedure naturally provides advantages. In general, extracorporeal therapies require dedicated time commitments from the patient, require medical personnel to provide vascular access and to run the equipment, and involve medical risks associated with that vascular access. By integrating the solute removal of the present invention with hemodialysis, no increase in overall treatment time and no additional requirements or risk is incurred over and above that associated with a hemodialysis treatment itself.

Because implementation of affinity membrane therapy requires access to the bloodstream, it may be particularly suited to patients who regularly undergo extracorporeal blood treatment such as hemodialysis. Furthermore, as discussed below, dialysis patients suffer from several medical conditions which may be ameliorated by treatment with affinity membrane devices. For patients in whom blood access is not readily available, usage of affinity membrane therapy would be limited to those medical conditions for which the benefits of treatment outweigh the risk of blood access. Examples of such non-dialysis applications are discussed in greater detail below.

By way of example and not limitation, an example of a method illustrating the use of the affinity membrane device of the present invention will now be given.

Prior to initiation of dialysis, surgery is performed to create a permanent blood access site (either a synthetic arteriovenous graft or an anastomosis, i.e., a surgical joining of an artery and a vein). Dialysis is typically performed using a two-needle procedure, with separate lines for withdrawal and return of blood. The affinity device is placed in series with the dialyzer, and it is primed with saline along with the rest of the dialysis circuit. The blood is anticoagulated according to the patient's usual anticoagulation regime. During dialysis, blood is pumped to the dialyzer at a flow rate of 200–500 ml/min using a peristaltic pump. Because the affinity membrane device is in series with the dialyzer, its blood flow rate is equal to the patient's prescribed blood flow rate for dialysis. To minimize variations from normal dialysis procedure, the affinity device is operated for the patient's usual dialysis treatment time, which is typically for three to four hours three times a week. Depending on the amount of target ligand to be removed, the affinity device may be used during some or all of the dialysis procedures.

By way of example and not limitation, examples of medical conditions of dialysis patients that may be improved by affinity membranes are amyloidosis, hypercholesterolemia, and transplant rejection.

Long-term dialysis patients suffer from joint pain and other symptoms of amyloidosis which are believed to be caused by long-term accumulation of beta-2 microglobulin in joints and other tissues. Beta-2 microglobulin is a low molecular weight protein that is normally shed from the cell membranes of all nucleated cells in the body. Normally, the kidney plays a critical role in removing excess beta-2 microglobulin from the plasma. In the absence of kidney function, the plasma concentration of beta-2 microglobulin gradually rises to up to 50 times its normal value. A high plasma concentration causes transport of beta-2 microglobulin into various tissues. For dialysis patients, periodic removal of beta-2 microglobulin by treatment with an affinity membrane would reduce the concentration of beta-2 microglobulin in the plasma. A lower average plasma concentration would reduce transport from plasma to the tissues, and possibly lead to removal from the tissue.

Cardiovascular disease, not renal disease, is the leading cause of death of dialysis patients. In the general population, a high LDL concentration is known to be a risk factor for cardiovascular disease. Since a substantial fraction of dialysis patients have high LDL levels, the inventors believe dialysis patients' high risk of cardiovascular morbidity and mortality is in part attributable to their high LDL levels. In patients with high LDL values, periodic removal of LDL by treatment with an affinity membrane during dialysis will reduce the LDL concentration, thereby reducing the risk of morbidity and mortality.

The typical kidney transplant recipient is maintained on dialysis for several months while waiting for a donor organ to become available. For allogeneic transplants (i.e. human organs for human recipients), removal of immunoglobulin G (IgG) may reduce the incidence and/or severity of acute organ rejection, thereby improving overall graft survival rates. Thus, use of an affinity membrane which removes IgG immediately prior to transplantation will reduce the IgG level at the time of transplantation, thereby reducing the risk of transplant rejection.

For patients in which permanent blood access is not available, temporary access to the bloodstream is established at a suitable location (e.g. by insertion of a dual-lumen catheter in the subclavian vein). The lumen side of the affinity device is connected to a peristaltic pump and primed with saline. After the lumen side is primed, the filtrate port will be opened to allow priming of the shell side. The filtrate line will then be clamped while the device is primed with blood. To prevent blood clotting, anticoagulant may be added as a bolus (by syringe or pump) at the start of the procedure and/or continuously throughout the procedure (by a pump). Because the blood flow rate will be limited by the capacity of the temporary access, the maximum blood flow rate will range from 100 to 300 ml/min. For operation in the embodiment of the present invention depicted in FIG. 2, the filtrate port will be opened after the blood fills the lumen side. Plasma and blood concentrations of the target will be reduced as described above. The procedure time and the frequency of use will depend on the amount of target ligand to be removed.

By way of example and not limitation, examples of three medical conditions of patients not on dialysis for which affinity membranes may be employed are severe hypercholesterolemia, transplant rejection, and autoimmune disease.

The most severe form of hypercholesterolemia is homozygous familial hypercholesterolemia. Left untreated, this disease normally proves fatal by age twenty. Whereas milder forms of hypercholesterolemia may not warrant invasive extracorporeal blood treatment, patients with homozygous familial hypercholesterolemia have previously been treated with complicated and expensive affinity column systems. Compared to affinity columns, affinity membranes offer the potential advantages of simplicity of operation and reduced cost. With the use of the affinity device, the inventors anticipate that reduced LDL levels will lead to increased life expectancy.

Like dialysis patients, other organ transplant recipients can benefit from removal of immunoglobulins prior to transplantation. As was discussed above, removal of immunoglobulin G (IgG) prior to allogeneic transplantations may reduce the incidence and/or severity of acute organ rejection, thereby improving overall graft survival rates. Given the tremendous shortage of human organs for transplantation, xenotransplantation (e.g. use of pig organs for human recipients) is currently under investigation. Removal of the subclass of immunoglobulin M responsive for hyperacute rejection (xenoreactive IgM) may be a key aspect of the success of xenotransplantation.

In autoimmune diseases such as systemic lupus erythematosus, a patient develops antibodies to his own cells. The multitude of symptoms of autoimmune disease may be attributed to the actions of autoantibodies on specific tissues or accumulation of immune complexes formed from those autoantibodies. Thus, removal of autoantibodies and/or immune complexes by use of an affinity membrane would reduce the symptoms and complications of autoimmune diseases. For autoimmune diseases which target the kidney, for example Goodpasture's Disease and systemic vasculitis, removal of autoantibodies would slow down progression of renal disease, postponing or preventing the need for dialysis.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A hollow fiber membrane comprising:
a plurality of elongated hollow fibers, each fiber having a peripheral wall surrounding a lumen, the peripheral wall having a plurality of pores extending therethrough, the number and configuration of the pores being effective to separate blood into plasma and cellular components, each pore having ligand bound to an internal surface and having a length dimension such that adequate surface area is provided for the attachment of the ligand to ensure that the ligands capture substantially all target molecules, the peripheral wall having a thickness ranging from approximately 300 to 3500 microns, and the hollow fibers having internal diameters of approximately 70 to 140 microns, and wherein the ligands are immobilized to the internal surface of the pores with polyethylene glycol having a chain length of about 50 to 250 carbon atoms.

2. The hollow fiber membrane of claim 1 wherein the hollow fibers are made of material selected from the group consisting of: cellulose triacetate; polysulfone; polyacrylonitrile; ethylene/vinyl alcohol copolymer; polymethylmethacrylate; polyamide; polypropylene; cellulose acetate; regenerated cellulose; polycarbonate, polyethylene; polyvinylalcohol; and polyvinylchloride.

3. The hollow fiber membrane of claim 1 wherein the ligands are also bound to the pores with an avidin/biotin molecular complex.

4. The hollow fiber membrane of claim 1 wherein the plurality of elongated hollow fibers are in a single bundle.

5. A method for reducing concentration levels of a target solute in a patient suffering from a medical condition characterized by excessive levels of the target solute comprising:

removing whole blood from the patient;

providing a hollow fiber membrane device having (a) an elongated housing with a single inlet port and a single outlet port for entry and exit of blood therefrom; and (b) hollow fibers encased inside the housing, the hollow fibers having a plurality of pores extending therethrough, the number and configuration of the pores effective to separate blood into plasma and cellular components, the pores having ligands bound to an internal surface of the pores, the ligands having an affinity for the target solute in the plasma, the ligands being immobilized to the internal surface of the pores with polyethylene glycol having a chain length of about 50 to 250 carbon atoms;

transporting the blood into the inlet port of the housing;

causing the plasma of the blood to flow into the pores of the hollow fibers by means of positive filtration created by a positive transmembrane pressure near the inlet port while not allowing the cellular components to flow into same;

contacting the target solute in the plasma with the ligands for a clinically significant period of time to substantially lower the concentration level of the target solute from the plasma;

causing non-targeted solute of the plasma to flow back through the pores of the hollow fibers by means of reverse filtration created by a negative transmembrane pressure near the outlet port to reunite the non-targeted solute with the cellular components of the blood to form a treated blood product; and infusing the treated blood product into the patient.

6. The method of claim 5 wherein the ligand is a polyclonal antibody.

7. The method of claim 5 wherein the ligand is an autoantigen capable of binding autoantibodies.

8. The method of claim 5 wherein the ligand is an enzyme.

* * * * *